United States Patent [19]

Sommargren

[11] Patent Number: 4,685,803
[45] Date of Patent: Aug. 11, 1987

[54] METHOD AND APPARATUS FOR THE MEASUREMENT OF THE REFRACTIVE INDEX OF A GAS

[75] Inventor: Gary E. Sommargren, Madison, Conn.

[73] Assignee: Zygo Corporation, Middlefield, Conn.

[21] Appl. No.: 821,773

[22] Filed: Jan. 23, 1986

[51] Int. Cl.4 .............................................. G01B 9/02
[52] U.S. Cl. ................................................... 356/361
[58] Field of Search ....................................... 356/361

[56] References Cited

FOREIGN PATENT DOCUMENTS 3401900 8/1985 Fed. Rep. of Germany ...... 356/361
2039382 8/1980 United Kingdom ................ 356/361
2120383 11/1983 United Kingdom ................ 356/361

*Primary Examiner*—Davis L. Willis
*Assistant Examiner*—Matthew W. Koren
*Attorney, Agent, or Firm*—Stiefel, Gross, Kurland & Pavane

[57] ABSTRACT

An optical apparatus capable of measuring the absolute refractive index of a gas is provided which comprises: (1) an evacuated cell (50) comprised, most preferably, of a bellows (52) with transparent plano windows (41, 61) which have diameters larger than the outside diameter of said bellows (52) attached to each end of said bellows (52); (2) means, most preferably, high reflectivity mirror coating spots (46, 47, 66, 67), for obtaining reflections from the surfaces on the vacuum sides of said windows (41, 61); (3) means for varying the distances between said high reflectivity mirror coatings from less than a few micrometers to approximately 100 millimeters; (4) means, most preferably a first differential plane mirror interferometer (23) with its measurement leg in the gas to be measured outside of the vacuum cell (50); means, most preferably a second differential plane mirror interferometer (33) with its measurement leg in the vacuum cell (50); (6) means, for measuring the first phase variation (73, 75, 77) in said first differential plane mirror interferometer (23) as said distance varies from zero to approximately 100 milimeters; (7) means, for measuring the second phase variation (83, 85, 87) in said second differential plane mirror interferometer (33) as said distance varies from zero to approximately 100 millimeters; (8) means, most preferably a microcomputer (90) for taking the ratio of said first and second phase variations to provide an output (92) which is the absolute index of refraction of the gas.

20 Claims, 4 Drawing Figures

METHOD AND APPARATUS FOR THE MEASUREMENT OF THE REFRACTIVE INDEX OF A GAS

BACKGROUND OF THE INVENTION

1. Field of the Invention

The present invention relates to a method and apparatus for the measurement of the refractive index of a gas. More particularly, the invention relates to optical apparatus which is useful for high accuracy displacement metrology using interferometry in ambient air.

2. The Prior Art

An interferometer is the basic instrument for most of the high-accuracy displacement measurements in the machine tool and semiconductor fabrication industries. One type of interferometer representative of the current state of the art is described in Bagley et al., U.S. Pat. No. 3,458,259 issued July 26, 1969. The absolute accuracy of interferometric displacement metrology is limited by two dominant factors: (1) the uncertainty in the vacuum wavelength of the light source, and (2) the uncertainty in the refractive index of the ambient air, see W. Tyler Estler, "High-Accuracy Displacement Interferometry in Air:," *Applied Optics*, vol. 24, pp. 808–815 (Mar. 15, 1985) and Farrand et al., U.S. Pat. No. 4,215,938 issued Aug. 5, 1980.

As noted in the aforementioned references, interferometric displacement measurements in air are subject to environmental uncertainties, particularly to changes in air pressure, temperature, humidity, and molecular composition. Such factors alter the wavelength of the light used to measure the displacement. Under normal conditions the refractive index of air is approximately 1.0003 with a variation of $\pm 10^{-4}$. In many applications the refractive index of air must be known with an error of less than $10^{-7}$ to $10^{-8}$.

One prior-art technique for correcting the environmental uncertainties is based on using individual sensors to measure the barometric pressure, temperature, and humidity, and, then, using these measurements to correct the measured displacement. The commercially available Automatic Compensator, Model 5510 Opt 010, from Hewlett-Packard uses this technique. This technique has been only partly satifactory due to the errors in the sensors and due to the errors arising from variations in the composition of the air, e.g., the percentage $CO_2$ content and presence of industrial gases, i.e. Freon and solvents are ignored in this technique.

A second prior-art technique is based on the aforementioned Farrand et al., U.S. Pat. No. 4,215,938 issued Aug. 5, 1980. This technique incorporates a rigid enclosure, the length of which must be accurately known, independent of environmental conditions and constant in time. The change in optical path length of this enclosure is measured as remotely controlled valves allow the enclosure to be evacuated and refilled with ambient air. The wavelength of the air in the enclosure is proportional to the measured change in optical path length. This technique has also been only partly satisfactory due to the fact that the characteristics of the air in the enclosure do not adequately represent those of the air in the measurement path, thusly systematic errors are introduced. It has been found that even with a perforated enclosure, serious systematic differences exist between the characteristics of the air inside of and external to the enclosure. In addition, the need for valves and a vacuum pump makes this technique awkward to implement for many applications.

Another prior-art technique incorporates a fixed length optical reference path which contains the ambient air. The technique measures the difference in optical length of the fixed length due to the variations in the refractive index of the ambient air. This technique is only partly satisfactory due to the fact that since it is differential it depends critically on the precise knowledge of the initial conditions.

Consequently, while prior-art techniques for measuring the refractive index of a gas are useful for some applications, none known to the applicant provide the technical performance in a commercially viable form for applications requiring the high accuracy interferometric measurement of displacement in air. The disadvantages of the prior-art apparatus are overcome by the present invention.

SUMMARY OF THE INVENTION

In accordance with the instant invention, optical apparatus capable of measuring the absolute refractive index of a gas is provided which comprises: (1) an evacuated cell comprised, most preferably, of a bellows with transparent plano windows which have diameters larger than the outside diameter of said bellows attached to each end of said bellows; (2) means, most preferably, high reflectivity mirror coating spots, for obtaining reflections from the surfaces on the vacuum sides of said windows; (3) means for varying the distance between said high reflectivity mirror coatings from less than a few micrometers to approximately 100 millimeters: (4) means, most preferably a first differential plane mirror interferometer with its measurement leg in the gas to be measured outside of the vacuum cell; (5) means, most preferably a second differential plane mirror interferometer with its measurement leg in the vacuum cell; (6) means, for measuring the first phase variation in said first differential plane mirror interferometer as said distance varies from zero to approximately 100 millimeters; (7) means, for measuring the second phase variation in said second differential plane mirror interferometer as said distance varies from zero to approximately 100 millimeters; (8) means, most preferably a microcomputer for taking the ratio of said first and second phase variations to provide an output which is the absolute index of refraction of the gas.

THE DRAWINGS

DETAILED DESCRIPTION OF THE INVENTION

Figure 1:
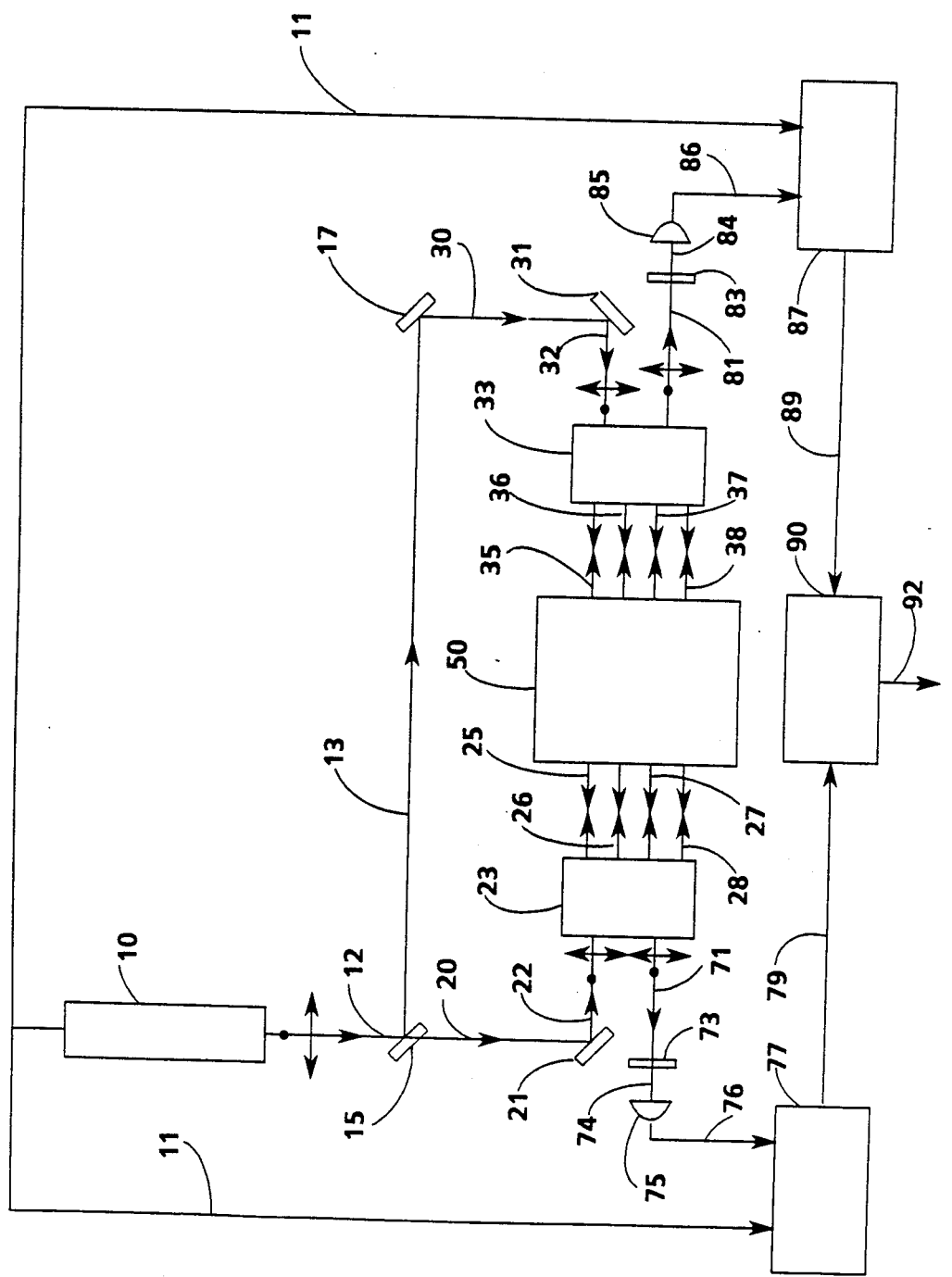
FIG. 1 depicts in schematic form one embodiment of the instant invention.

FIG. 1 depicts in schematic form one embodiment of the instant invention. While the apparatus has application for a wide range of radiation sources, the following is taken by way of example with respect to an optical measuring system. Light source (10), which most preferably uses a laser, emits beam (12) comprised of two frequency components $f_1$ and $f_2$ which are orthogonally polarized as indicated by the dot and arrow, see for example, Bagley et al. U.S. Pat. No. 3,458,259 issued July 26, 1969, and commonly owned copending U.S. Patent applications Ser. Nos. 710,859, 710,928, and 710,927. Beam (12) is divided equally by beamsplitter (15) into beams (13) and (20). Beam (13) is reflected by mirror (17) to become beam (30). Beams (20) and (30) are reflected by mirrors (21) and (31) to become beams (22) and (32), respectively. Beams (22) and (32) are incident on differential plane mirror interferometers (23) and (33), respectively. A differential plane mirror interferometer can take several forms, one of which is described in R. R. Baldwin and G. J. Siddall, "A double pass attachment for the linear and plane interferometer," *Proc. SPIE*, Vol. 480, pp. 78–83 (May 1984). Another form is described with reference to FIG. 2.

A differential plane mirror interferometer measures the optical path changes between two external plane mirrors. In addition, it is insensitive to thermal and mechanical disturbances that may occur in the interferometer beamsplitting cube and associated optical components. Differential plane mirror interferometer (23) has four exit/return beams (25), (26), (27), and (28). Beams (25) and (28), which comprise one measurement leg, are of optical frequency, $f_1$, and beams (26) and (27), which comprise the second measurement leg, are of optical frequency, $f_2$. Likewise, differential plane mirror interferometer (33) has four exit/return beams (35), (36), (37), and (38). Beams (35) and (38), which comprise one measurement leg, are of optical frequency, $f_1$ and beams (36) and (37), which comprise the second measurement leg, are of optical frequency, $f_2$.

Figure 3:
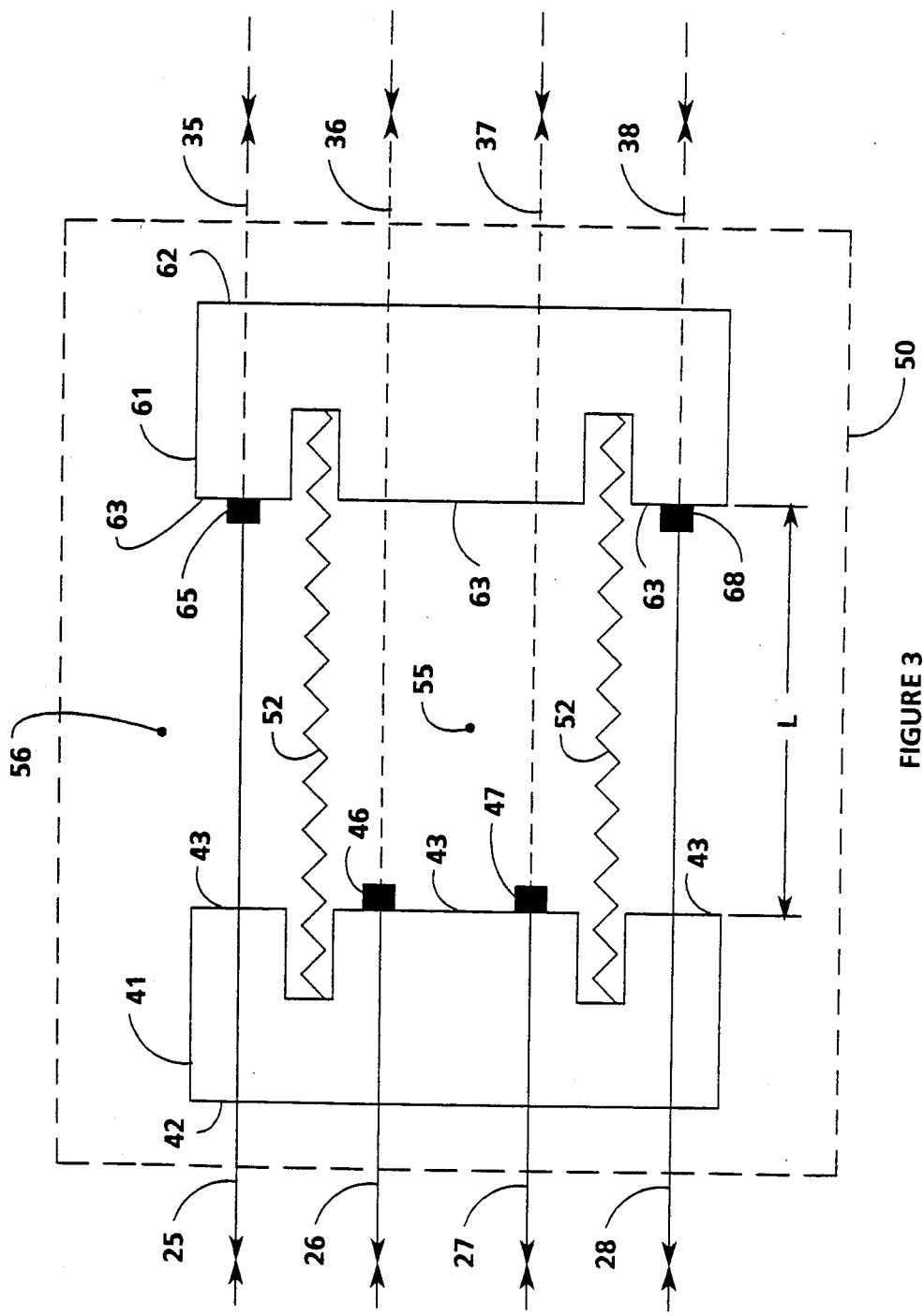
FIG. 3 depicts in schematic form one embodiment of the refractive index measurement cell used in FIG. 1.

Beams (25), (26), (27), and (28) are incident on refractive index measurement cell (50), described in detail in FIG. 3, which results in beam (71) leaving differential plane mirror interferometer (23). Beam (71) has both frequency components, $f_1$ and $f_2$, which are orthogonally polarized. Beam (71) contains information about the optical path length through the gas whose index of refractive is to be determined. Likewise, beams (35), (36), (37), and (38) are incident on refractive index measurement cell (50), which results in beam (81) leaving differential plane mirror interferometer (33). Beam (81) has both frequency components which are orthogonally polarized. Beam (81) contains information about the optical path length through a vacuum which serves as an absolute reference for the refractive index measurement. Beams (71) and (81) pass through polarizers (73) and (83), respectively, oriented at 45° to each polarization component, which mix the two orthogonally polarized frequency components to give beams (74) and (84), respectively. The interference between the two components is detected by photodetectors (75) and (85) as sinusoidal intensity variations with a frequency equal to the difference frequency, $f_2-f_1$. Sinusoidal electrical output (76) of photodetector (75) is compared to sinusoidal electrical reference signal (11) by phase meter /accumulator (77), see, for example, commonly owned, copending U.S. patent application, Ser. No. 710,928, to measure their phase difference (79) which is directly proportional to the optical path length through the gas whose refractive index is to be determined. This measured phase difference (79) can be expressed as, $$M_{gas}=4nL,$$

where n is the refractive index of the gas and 4L is the total physical length change experienced by beams (25), (26), (27), and (28). Likewise, sinusoidal electrical output (86) of photodetector (85) is compared to the same sinusoidal electrical reference signal (11) by phase meter/accumulator (87) to measure their phase difference (89) which is directly proportional to the optical path length through a vacuum whose refractive index is exactly unity. This measured phase difference (89) can be expressed as, $$M_{vac}=4L$$

where 4L is the total physical length change experienced by beams (35), (36), (37), and (38).

The ratio between measured phase differences (79) and (89) is calculated by microcomputer (90) as, $$M_{gas}/M_{vac}=4nL/4L=n$$

which gives output (92), the refractive index, n, of the gas.

Figure 2:
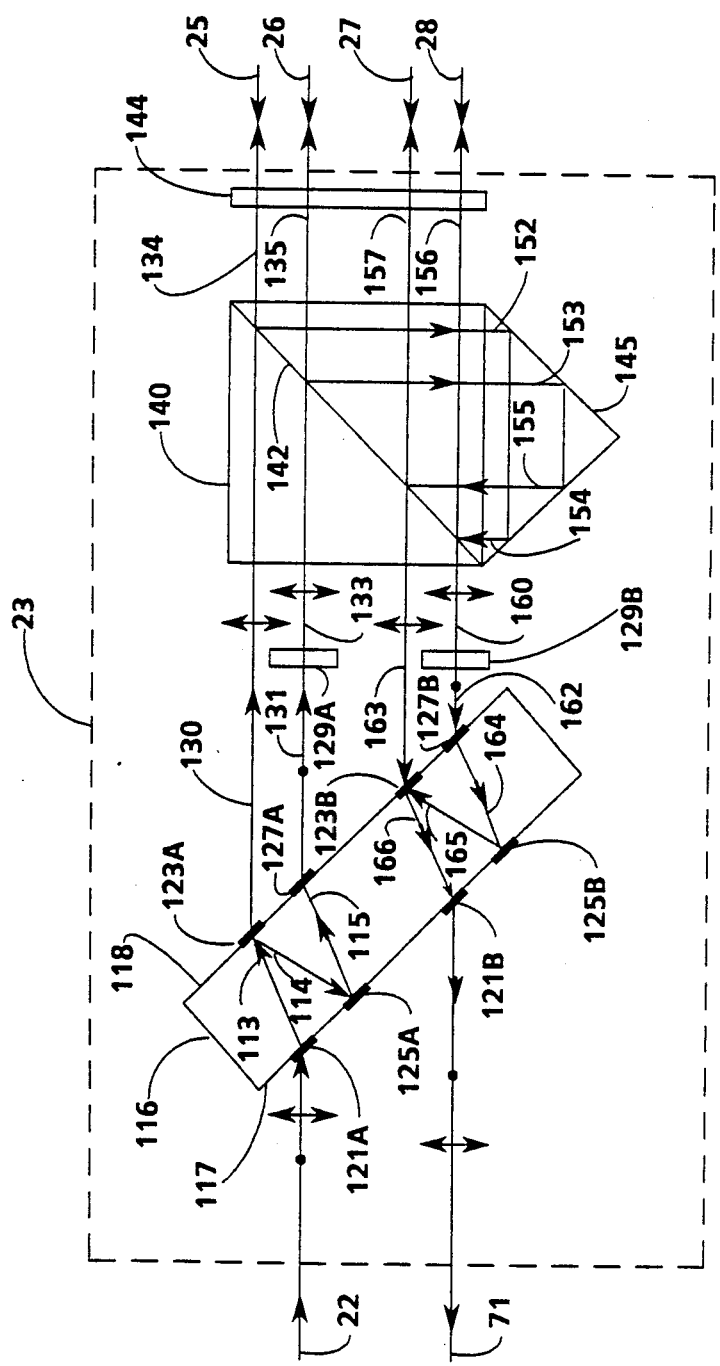
FIG. 2 depicts one form of a differential plane mirror interferometer used in FIG. 1.

FIG. 2 depicts in schematic form one embodiment of the differential plane mirror interferometer (23) shown in FIG. 1. It operates in the following way: Beam (22) is incident on shear plate (116) which is a tilted glass substrate with optically flat surfaces (117) and (118) which are mutually parallel. The function of shear plate (116) is to spatially separate the two frequency components using conventional polarization techniques. Beam (22) passes through surface (117) to become beam (113) which has the same polarization as beam (22). Surface (117) has an antireflection coating (121A) over the region where beam (22) passes through it. Polarizing coating (123A) on surface (118) splits beam (113) so that one polarized frequency component is transmitted as beam (130) whereas the other orthogonally polarized frequency component is reflected as beam (114). Beam (114) is totally reflected from reflective coating (125A) on surface (117) to become beam (115). Beam (115) passes through surface (118) to become beam (131) which has the same polarization as beam (115). Surface (118) has an antireflection coating (127A) over the region where beam (115) passes through it.

Beam (131) passes through half-wave retardation plate (129A) which rotates the linear polarization of beam (131) by 90° so that resultant beam (133) has the same polarization (but still a different frequency) as beam (130). Beams (130) and (133) enter polarizing beamsplitter (140) with polarizing coating (142) and are transmitted as beams (134) and (135) respectively. Beams (134) and (135) pass through quarter-wave retardation plate (144) and are converted into circularly polarized beams (25) and (26), respectively. Beams (25) and (26) are reflected back on themselves by mirrors within cell (50) and pass back through quarter-wave retardation plate (144) and are converted back into linearly polarized beams that are orthogonally polarized to the original incident beams (134) and (135). These beams are reflected by polarizing coating (142) to become beams (152) and (153). Beams (152) and (153) are reflected by retroreflector (145) to become beams (154) and (155). Beams (154) and (155) are reflected by polarizing coating (142) to become beams (156) and (157). Beams (156) and (157) pass through quarter-wave retardation plate (144) and are converted into circularly polarized beams (28) and (27), respectively.

Beams (28) and (27) are reflected back on themselves by the same mirrors within cell (50) and pass back through quarter-wave retardation plate (144) and are converted back into linearly polarized beams that are polarized the same as the original incident beams (134) and (135). These beams are transmitted by polarized coating (142) and leave polarizing beamsplitter (140) as beams (160) and (163). Beams (160) and (163) are mutually parallel by virtue of the inherent optical properties of retroreflector (145), independent of any tilt that may be present between the mirrors in cell (50). Beam (160) passes through half-wave retardation plate (129B) which rotates the linear polarization of beam (160) by 90° so that resultant beam (162) has a linear polarization which is orthogonal to beam (163). Beam (162) passes through surface (118) to become (164) which has the same polarization as beam (162). Surface (118) has an antireflection coating (127B) over the region where beam (162) passes through it. Beam (164) is totally reflected from reflective coating (125B) on surface (117) to become beam (165). Beams (165) and (163) are recombined to form beam (166) by polarizing coating (123B) over the region where beams (165) and (163) intersect. Beam (166) passes through surface (117) to become beam (71). Surface (117) has an antireflection coating (121B) over the region where beam (166) passes through it.

Beam (71), like input beam (22), has two frequency components which are orthogonally polarized. Each frequency component has traversed exactly the same optical path length (through air and glass) except for an optical path difference through the gas in cell (50). Thus, beam (71) contains information about the optical path length through the gas whose index of refraction is to be determined. Differential plane mirror interferometer (33) is a mirror image of (23) and operates in an analogue way.

FIG. 3 depicts in schematic form one embodiment of the refractive index measurement cell (50) shown in FIG. 1. Cell (50) is composed of two glass substrates (41) and (61) with optically flat and parallel surfaces (42) and (43), and (62) and (63), respectively, each sealed to one end of cylindrical bellows (52). Volume (55) is a vacuum with a pressure of less than $10^{-4}$ mm Hg. Surface (43) has two opaque, highly reflecting coatings (46) and (47) near its center while surface (63) has two opaque highly reflecting coatings (65) and (68) near its periphery. In use, cell (50) measures the refractive index, n, of surrounding gas (56) as follows: First substrates (41) and (61) are brought close together so that L=0, i.e. L≦a few micrometers. It should be noted that the thickness of coatings (46), (47), (65), and (68) is of the order of one micrometer.

In this condition, beams (25) and (28) of optical frequency $f_1$ reflecting from coatings (65) and (68), respectively, travel the same optical path length as beams (26) and (27) of optical frequency $f_2$ reflecting from coatings (46) and (47), respectively. Likewise, beams (35) and (38) of optical frequency $f_1$ reflecting from coatings (65) and (68), respectively, travel the same optical path length as beams (36) and (37) of optical frequency $f_2$ reflecting from coatings (46) and (47). Phase meters/accumulators (77) and (87) shown in FIG. 1, are then initialized, i.e., zeroed. Substrates (41) and (61) are then pulled apart to a separation, L. It is not necessary to know the value of L but the accuracy of determining the refractive index, n, is greater for larger values of L. For example, to determine n to 1 part in $10^8$, L should be greater than 100 mm when the phase resolution of phase meters/accumulators (77) and (87) is 1°. Beams (25) and (28) reflecting from coatings (65) and (68), respectively, now travel a total additional optical path length through surrounding gas (56) of 4nL as compared to beams (26) and (27) reflecting from coatings (46) and (47), respectively. This is indicated as measurement (79) in FIG. 1. Beams (36) and (37) reflecting from coatings (46) and (47), respectively, now travel a total additional optical path length through vacuum (55) of only 4L as compared to beams (35) and (38) reflecting from coatings (65) and (68), respectively. This is indicated as measurement (89) in FIG. 1. The ratio, output (92), between measured (79) and (89), as calculated by microcomputer (90), is the refractive index, n.

This embodiment is preferred because the inherent symmetry of the beams in cell (50) makes the measurement of the refractive index less susceptible to thermal instabilities in substrates (41) and (61). Under certain circumstances where lower cost is desirable, the optical and electronic components (specifically items (15), (17), (31), (33), (83), (85), and (87)) that are needed to make measurement (89), $M_{vac}$ (which in essence is a measurement of L), may be eliminated if the value of L is determined by some other means.

Figure 4:
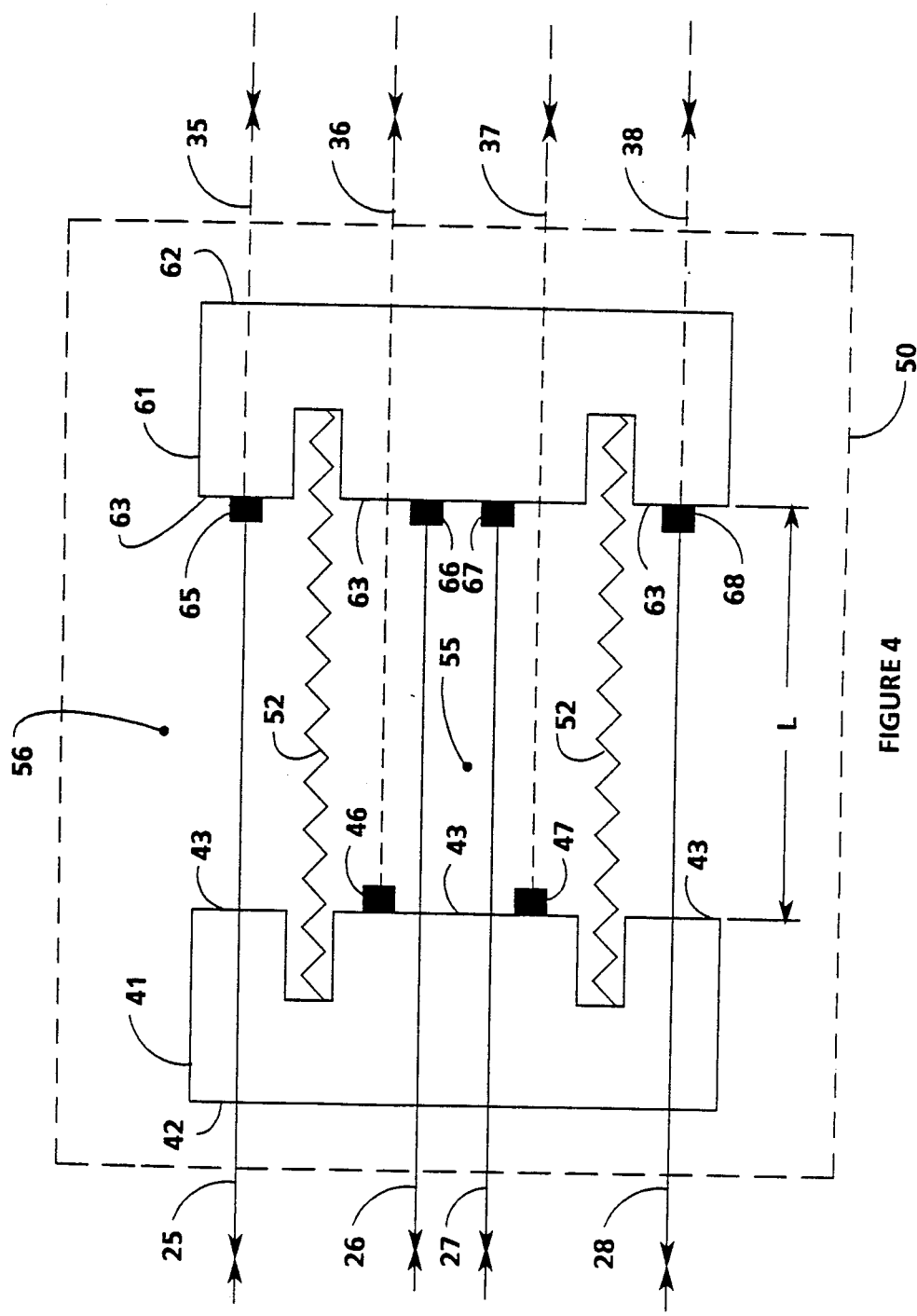
FIG. 4 depicts in schematic form a second embodiment of the refractive index measurement cell used in FIG. 1.

FIG. 4 depicts in schematic form a second embodiment of refractive index measurement cell (50) shown in FIG. 1 which is a modification of cell (50) detailed in FIG. 3. The modifications are the addition of two opaque, highly reflecting coatings (66) and (67) near the center of surface (63), and the slight offset of beams (26) and (27) so that they reflect from coatings (66) and (67), instead of coatings (46) and (47), respectively. The operation of cell (50) is identical to that just described in FIG. 3 except that beams (25) and (28) reflecting from coatings (65) and (68), respectively, now travel a total additional optical path length of 4(n−1)L as compared to beams (26) and (27) reflecting from (66) and (67), respectively. This changes measured phase difference (79) to $M_{gas\text{-}vac}=4(n-1)L$ so that the ratio between measured phase differences (79) and (89), as calculated by microcomputer (90), is $$M_{gas\text{-}vac}/M_{vac}=4(n-1)/4L=n-1$$

The resultant output (92) is then given by, $$N=1+M_{gas\text{-}vac}/M_{vac}$$

This second embodiment of cell (50), because of the asymmetry of the beams, is more susceptible to thermal instabilities in substrates (41) and (61). However, under some circumstances where lower cost is desirable, the optical and electronic components that are needed to make measurement (89), $M_{vac}$ (which in essence is a measurement of L), may be eliminated if the value of L is measured by some other means. In this case the precision to which L must be measured is four orders of magnitude less stringent than if the measurement (89), $M_{vac}$, in the first embodiment of cell (50) in FIG. 3 is eliminated.

The principal advantages of the instant invention are: (1) increased measurement accuracy, (2) no errors are introduced due to variations in the composition of the gas, and (3) the gas to be measured need not be in an enclosed or ventilated sample chamber.

While a preferred embodiment of the invention has been disclosed, obvious modifications can be made therein, without departing from the scope of the invention as defined in the following claims.

I claim:

1. An optical apparatus for measuring the absolute refractive index "n" of a gas, said apparatus comprising a light source and a vacuum cell optically aligned therewith and spatically separated therefrom, said cell comprising a pair of inner optically reflective surfaces separable by a distance "L" and means for varying said distance "L" varying the optical path length of light travel within said cell; first differential plane mirror interferometer means optically spaced between said light source and said vacuum cell and in optical alignment therewith, said first interferometer means having a first associated measurement leg optically disposed outside of said vacuum cell and in said gas to be measured; second differential plane mirror interferometer means optically spaced between said light source and said vacuum cell in optical alignment therewith, said second interferometer means having a second associated measurement leg optically disposed in said vacuum cell; first means optically connected to said first interferometer means for receiving an output therefrom for measuring a first phase variation in said first differential plane mirror interferometer means output for providing a first phase variation value as said distance "L" varies; second means optically connected to said said second interferometer means for receiving an output therefrom for providing a second phase variation value in said second differential plane mirror interferometer means output as said distance "L" varies; and means operatively connected to said first and second phase variation value providing means for receiving said first and second variation values and taking the ratio thereof for providing an output therefrom which is the absolute index of refraction "n" of said gas, said first and second differential plane mirror interferometer means being optically aligned with an input beam emitted from said light source, said first and second associated measurement legs having associated output beams, said pair of inner optically reflective surfaces being optically aligned with said associated output beams.

2. An apparatus in accordance with claim 1 wherein said cell further comprises a bellows having said pair of windows, said windows comprising transparent plano windows having diameters larger than the outside diameter of said bellows attached to each end of said bellows, one said pair of windows optically reflective surface comprising two high reflectivity mirror coating spots disposed for obtaining reflections from said one surface on the vacuum side of said transparent plano window and within the diameter of said bellows, the other of said pair of windows optically reflective surface comprising two high reflectivity mirror coating spots disposed for obtaining reflections from said other window reflective surface on the vacuum side of said other transparent plano window and outside the diameter of said bellows.

3. An apparatus in accordance with claim 2 wherein said distance varying means comprises means for varying said distance "L" between said highly reflective mirror coatings substantially between 0 and 100 millimeters.

4. An apparatus in accordance with claim 3 wherein said ratio taking means comprises a microcomputer.

5. An apparatus in accordance with claim 4 wherein said light source comprises a laser.

6. An apparatus in accordance with claim 5 wherein said emitted light comprises a beam having a pair of orthogonally polarized frequency components which are optically provided to said differential plane mirror interferometers for providing a plurality "N" of associated exit/return beams to said cell for each of said first and second differential plane mirror interferometer.

7. An apparatus in accordance with claim 6 wherein said first phase variation value providing means comprises first phase meter/accumulator means for providing a measured phase difference of $M_{gas}=NnL$ where n is the refractive index of gas and NL is the total physical length change through said gas experienced by said exit/return beams associated with said first differential plane mirror interferometer, said second phase variation value providing means providing a phase difference of $M_{vac}=NL$ as a known value, said ratio of said measured phase differences being $M_{gas}/M_{vac}=NnL/NL=n$ for providing said refractive index n of said gas as said output as $n=M_{gas}/M_{vac}$.

8. An apparatus in accordance with claim 7 wherein $N=4$.

9. An apparatus in accordance with claim 6 wherein said first phase variation value providing means comprises first phase meter/accumulator means for providing a measured phase difference of $M_{gas}=NnL$ where n is the refractive index of the gas and NL is the total physical length change through said gas experienced by said exit/return beams associated with said first differential plane mirror interferometer, said second phase variation value providing means comprising second phase meter/accumulator means for providing a measured phase difference of $M_{vac}=NL$ where NL is the total physical length change through said vacuum experienced by said exit/return beams associated with said second differential plane mirror interferometer, said ratio of said measured phase differences being $M_{gas}/M_{vac}=NnL/NL=n$ for providing said refractive index n of said gas as said output as $n=M_{gas}/M_{vac}$.

10. An apparatus in accordance with claim 9 wherein $N=4$.

11. An optical apparatus for measuring the absolute refractive index "n" of a gas, said apparatus comprising a light source and a vacuum cell optically aligned therewith and spatially separated therefrom, said cell comprising a pair of windows, said windows comprising a pair of inner optically reflective surfaces separable by a distance "L" and means for varying said distance "L" for varying the optical path length of light travel within said cell; first differential plane mirror interferometer means optically spaced between said light source and said vacuum cell and in optical alignment therewith, said first interferometer means having a first associate measurement leg optically disposed substantially equally in both said vacuum cell and outside of said vacuum cell in said gas to be measured; second differential plane mirror interferometer means optically spaced between said light source and said vacuum cell in optical alignment therewith, said second interferometer means having a second associated measurement leg optically disposed in said vacuum cell; means optically connected to said first interferometer means for receiving an output therefrom for measuring a first phase variation in said first differential plane mirror interferometer means output for providing a first phase variation value as said distance "L" varies; second means optically connected to said second interferometer means for receiving an output therefrom for providing a second phase variation value in said second differential plane mirror interferometer means output as said distance "L" varies; and means operatively connected to said first and second phase variation value providing means for receiving said first and second phase variation values and taking the ratio thereof for providing an output therefrom which is the absolute index of refraction of said gas minus one, represented by n-1, said first and second differential plane mirror interferometer means being optically aligned with an input beam emitted from said light source, said first and second associated measurement legs having associated output beams, said pair of inner optically reflective surfaces being optically aligned with said associated output beams.

12. An apparatus in accordance with claim 11 wherein said cell further comprises a bellows having said pair of windows, said windows comprising transparent plano windows having diameters larger than the outside diameter of said bellows attached to each end of said bellows, one of said pair of windows optically reflective surface comprising two high reflectivity mirror coating spots disposed for obtaining reflections from said one surface on the vacuum side of said transparent plano window and within the diameter of said bellows, the other of said pair of windows optically reflective surface comprising two high reflectivity mirror coating spots disposed for obtaining reflections from said other window reflective surface on the vacuum side of said other transparent plano window and outside the diameter of said bellows and two high reflectivity mirror coating spots disposed for obtaining reflections from said other window reflective surface on the vacuum side of said other transparent plano window and within the diameter of said bellows.

13. An apparatus in accordance with claim 12 wherein said distance varying means comprises means for varying said distance "L" between said highly reflective mirror coatings substantially between 0 and 100 millimeters.

14. An apparatus in accordance with claim 13 wherein said ratio taking means comprises a microcomputer.

15. An apparatus in accordance with claim 14 wherein said light source comprises a laser.

16. An apparatus in accordance with claim 15 wherein said emitted light comprises a beam having a pair of orthogonally polarized frequency components which are optically provided to said differential plane mirror interferometers for providing a plurality "N" of associated exit/return beams to said cell for each of said first and second differential plane mirror interferometer.

17. An apparatus in accordance with claim 16 wherein said first phase variation value providing means comprises first phase meter/accumulator means for providing a measured phase difference of $M_{gas-vac} = (n-1)NL$ where n is the refractive index of the gas and NL is the total physical length change through said gas experienced by said exit/return beams associated with said first differential plane mirror interferometer, said second phase variation value providing means comprising second phase meter/accumulator means for providing a measured phase difference of $M_{vac} = NL$ where NL is the total physical length change through said vacuum experienced by said exit/return beams associated with said second differential plane mirror interferometer, said ratio of said measured phase differences being $M_{gas-vac}/M_{vac} = (n-1)NL/NL = n-1$ for providing said refractive index n of said gas as said output as $n = 1 + M_{gas-vac}/M_{vac}$.

18. An apparatus in accordance with claim 17 wherein N=4.

19. An apparatus in accordance with claim 16 wherein said first phase variation value providing means comprises first phase meter/accumulator means for providing a measured phase difference of $M_{gas-vac} = (n-1)NL$ where n is the refractive index of the gas and NL is the total physical length change through said gas and vacuum experienced by said exit/return beams associated with said first differential plane mirror interferometer, said second phase variation value providing means providing a phase difference of $M_{vac} = NL$ as a known value, said ratio of said measured phase differences being $M_{gas-vac}/M_{vac} = (n-1)NL/NL = n-1$ for providing said refractive index n of said gas as said output as $n = 1 + M_{gas-vac}/M_{vac}$.

20. An apparatus in accordance with claim 19 wherein N=4.

* * * * *

UNITED STATES PATENT AND TRADEMARK OFFICE
CERTIFICATE OF CORRECTION

PATENT NO. : 4,685,803

DATED : August 11, 1987

INVENTOR(S) : Gary E. Sommargren

It is certified that error appears in the above-identified patent and that said Letters Patent is hereby corrected as shown below:

Column 2, line 33, change "millimeters:" to --millimeters;--.

Column 7, line 30, after "second" insert --phase--.

Signed and Sealed this

Fourth Day of April, 1989

Attest:

DONALD J. QUIGG

Attesting Officer

Commissioner of Patents and Trademarks